US011967005B2

(12) United States Patent
Brown

(10) Patent No.: US 11,967,005 B2
(45) Date of Patent: Apr. 23, 2024

(54) CONE BEAM ARTIFACT CORRECTION FOR GATED IMAGING

(71) Applicant: KONINKLIJKE PHILIPS N.V., Eindhoven (NL)

(72) Inventor: Kevin Martin Brown, Chardon, OH (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 350 days.

(21) Appl. No.: 17/608,622

(22) PCT Filed: May 6, 2020

(86) PCT No.: PCT/EP2020/062480
§ 371 (c)(1),
(2) Date: Nov. 3, 2021

(87) PCT Pub. No.: WO2020/229237
PCT Pub. Date: Nov. 19, 2020

(65) Prior Publication Data
US 2022/0215602 A1    Jul. 7, 2022

Related U.S. Application Data

(60) Provisional application No. 62/845,927, filed on May 10, 2019.

(51) Int. Cl.
G06K 9/00         (2022.01)
G06T 11/00        (2006.01)
(Continued)

(52) U.S. Cl.
CPC ............ *G06T 11/008* (2013.01); *G06T 15/08* (2013.01); *G16H 30/40* (2018.01); *G06T 2210/41* (2013.01)

(58) Field of Classification Search
CPC ... G06T 11/008; G06T 15/08; G06T 2210/41; G06T 11/006; G16H 30/40
See application file for complete search history.

(56) References Cited

U.S. PATENT DOCUMENTS 7,027,552 B2     4/2006  Shechter
9,087,404 B2 *   7/2015  Hansis ............... G06T 11/008
(Continued)

FOREIGN PATENT DOCUMENTS

EP        1643446 A1      4/2006
WO   WO-2006116316 A2 * 11/2006 ............. A61B 6/027
(Continued)

OTHER PUBLICATIONS

PCT International Search Report, International application No. PCT/EP2020/062480, dated Aug. 3, 2020.
(Continued)

*Primary Examiner* — Xin Jia
(74) *Attorney, Agent, or Firm* — Larry Liberchuk

(57) ABSTRACT

A system includes a reconstructor (314) configured to reconstruct cone beam projection data to generate cone beam artifact corrected short scan cone beam volumetric image data. A method includes reconstructing, with a reconstructor, cone beam projection data to generate cone beam artifact corrected short scan cone beam volumetric image data. A computer-readable storage medium storing computer executable instructions which when executed by a processor of a computer cause the processor to: reconstruct cone beam projection data to generate cone beam artifact corrected short scan cone beam volumetric image data.

12 Claims, 7 Drawing Sheets

(51) Int. Cl.
    *G06T 15/08*     (2011.01)
    *G16H 30/40*     (2018.01)

(56) References Cited

U.S. PATENT DOCUMENTS

| | | | |
|---|---|---|---|
| 2009/0028288 | A1 | 1/2009 | Horiuchi |
| 2012/0308102 | A1 | 12/2012 | Pack |
| 2013/0315453 | A1 | 11/2013 | Cao |
| 2016/0253818 | A1* | 9/2016 | Tang .................. G06T 5/50 |
| | | | 382/131 |
| 2016/0367212 | A1* | 12/2016 | Tang ................... A61B 6/5205 |

FOREIGN PATENT DOCUMENTS

| | | | | |
|---|---|---|---|---|
| WO | WO-2011002442 A1 | * | 1/2011 | ........... G06T 11/006 |
| WO | WO2018115025 A1 | | 6/2018 | |

OTHER PUBLICATIONS

Wesarg S. et al., "Parker Weights Revisited", Medical Physics, AIP, Melville, NY, US, vol. 29, No. 3, Mar. 2002, pp. 372-378, XP012011740.

Kudo H. et al., "New Approximate Filtered Backprojection Algorithm for Helical Cone-Beam CT with Redundant Data", 2003 IEEE Nuclear Science Symposium Conference Record. / 2003 IEEE Nuclear Science Symposium and Medical Imaging Conference, Oct. 19, 2003, pp. 3211-3215, XP010742770.

Xia Y. et al., "Truncation Correction Using a 3D Filter for Cone-Beam CT", Fully3D, Ed., Fully3D 2013, pp. 118-121, 2013.

Koken P. et al., "Aperture Weighted Cardiac Reconstruction for Cone-Beam CT", Physics in Medicine and Biology, 51(14), 3433-3448, 2006.

* cited by examiner

CONE BEAM ARTIFACT CORRECTION FOR GATED IMAGING

FIELD OF THE INVENTION

The following generally relates to imaging and more particularly to cone beam artifact correction for gated imaging and is described with particular application to computed tomography (CT).

BACKGROUND OF THE INVENTION

Cone beam artifacts can occur in different types of imaging situations in wide coverage computed tomography (CT) systems. One type of cone beam artifact occurs when the X-ray source path meets the criteria for an exact reconstruction (i.e. the source path crosses all planes containing an image point to be reconstructed), but more data is desired to be backprojected than is needed by the exact reconstruction algorithm, e.g., to improve the dose utilization of the scan. This type of cone beam artifact can be corrected, e.g., as described in U.S. Pat. No. 7,027,552 B2, which is incorporated herein by reference in its entirety, and/or otherwise.

A different situation occurs in scans where the source path does not cross all planes containing an object point to be reconstructed and an exact reconstruction is not possible. An example is illustrated in FIG. 1, for a gated short (i.e. less than 360-degrees) axial scan, where source locations 102 (the thicker open arc) on only a sub-portion of a circular path 104 (the thinner closed loop) of an X-ray source 106 that correspond to a desired cardiac phase to reconstruct do not cross an imaging plane 108 (i.e. all object points in the plane cannot be reconstructed exactly). Such a short scan has been used when scanning a moving object like the heart to mitigate blur and improve temporal resolution.

In general, a short-scan axial reconstruction generates a reconstruction with appropriate weighting for direct current (DC) frequencies along the (z) axis of rotation, but due to the variation of the cone angle of the rays used in backprojecting into a particular voxel, higher frequencies along the (z) axis of rotation are not weighted properly in all regions of the three-dimensional (3-D) Fourier domain. This mis-weighting of certain frequencies manifests as cone beam artifacts in images from these type of reconstructions. An example of such cone beam artifacts is shown in FIG. 2, which shows an axial image 202 with cone beam artifacts 204. In FIG. 2, the artifact manifests as a bright shading artifact. Examples of other artifacts include a dark shading and/or streaking.

Unfortunately, because the mis-weighting is different for each voxel, it is difficult to formulate an efficient short-scan reconstruction algorithm that mitigates these artifacts, and image quality may be degraded.

SUMMARY OF THE INVENTION

Aspects described herein address the above-referenced problems and/or others.

For instance, the following describes an approach for correcting certain cone beam artifacts.

In one aspect, a system includes a reconstructor configured to reconstruct cone beam projection data to generate cone beam artifact corrected short scan cone beam volumetric image data.

In another aspect, a method includes reconstructing, with a reconstructor, cone beam projection data to generate cone beam artifact corrected short scan cone beam volumetric image data.

In another aspect, a computer-readable storage medium stores instructions that when executed by a processor of a computer cause the processor to: reconstruct cone beam projection data to generate cone beam artifact corrected short scan cone beam volumetric image data.

Those skilled in the art will recognize still other aspects of the present application upon reading and understanding the attached description.

BRIEF DESCRIPTION OF THE DRAWINGS

The invention may take form in various components and arrangements of components, and in various steps and arrangements of steps. The drawings are only for purposes of illustrating the embodiments and are not to be construed as limiting the invention.

DETAILED DESCRIPTION OF EMBODIMENTS

The following describes an approach for correcting certain cone beam artifacts using a spatially variant 3D filter that corrects frequency mis-weighting in reconstructed volumetric image data.

Figure 3:
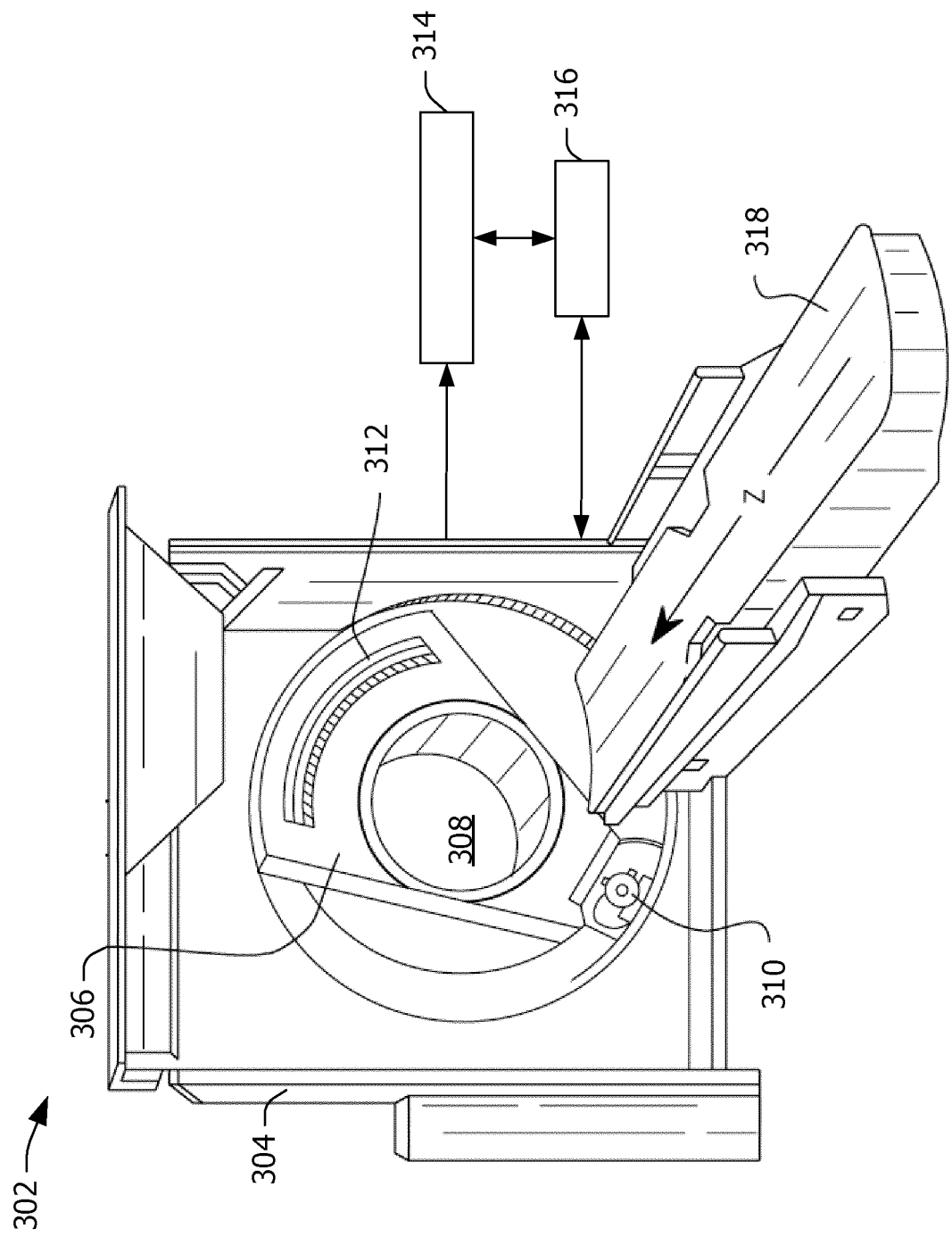
FIG. 3 diagrammatically illustrates an example imaging system with a reconstructor configured to correct for cone beam artifact with a 3-D spatially variant filter, in accordance with an embodiment(s) herein.

FIG. 3 diagrammatically illustrates an imaging system 302 such as a computed tomography (CT) scanner. The scanner 302 includes a stationary gantry 304 and a rotating gantry 306, which is rotatably supported by the stationary gantry 304 and rotates around an examination region 308 about a longitudinal or z-axis ("Z").

An X-ray radiation source 310, such as an X-ray tube, is supported by and rotates with the rotating gantry 306 around the examination region 308. The X-ray radiation source 310 emits X-ray radiation that is collimated e.g., by a source collimator (not visible) to form a generally cone, fan, wedge, or other shaped X-ray radiation beam that traverses the examination region 308.

A radiation sensitive detector array 312 subtends an angular arc opposite the radiation source 310 across the examination region 308. The detector array 312 includes one or more rows of detectors that are arranged with respect to each other along the z-axis direction and detects X-ray radiation traversing the examination region 308. The radiation sensitive detector array 312 detects radiation traversing the examination region 308 (and an object or subject therein) and produces projection data (line integrals) indicative of the detected radiation.

In one instance, the projection data is from a 360-degree axial scan. In another instance, the projection data is from a less than 360-degree axial scan (i.e. a short scan), such as a 320-degree axial scan (180-degree plus a beam angle). In another instance, the projection data is from an axial scan greater than 360-degrees. In another instance, the projection data is from an axial scan less than 320-degrees. In another instance, the projection data is from an axial between 320-degrees and 360-degrees.

A reconstructor 314 is configured to reconstruct the projection data to generate volumetric image data. In one instance, the reconstructor 314 is configured to correct cone beam projection data for certain cone beam artifacts, e.g., in scans where the variation of the cone angle of the rays used in backprojecting into a particular voxel results in higher frequencies along the (z) axis of rotation not being weighted properly in all regions of the 3-D Fourier domain where the mis-weighting of certain frequencies manifests as cone beam artifacts in the reconstructed volumetric image data. This includes correcting cone beam projection data for a 360-degree scan, a less than 360-degree scan, and/or other scan. As described in greater detail below, in one instance the reconstructor 314 employs a spatially variant 3D filter that corrects frequency mis-weighting in reconstructed volumetric image data and hence the cone beam artifacts in the volumetric image data resulting therefrom.

In one instance, the reconstructor 314 is implemented with hardware such as a central processing unit (CPU), a microprocessor (μCPU), a graphics processing unit (GPU), an application specific integrated circuit (ASIC), etc. configured to execute computer executable instructions on computer readable storage medium (which excludes transitory medium), such as physical memory and/or other non-transitory memory. The reconstructor 314 can be part of the system 302 (as shown) and/or remote therefrom.

A console 316 includes a human readable output device such as a display monitor, a filmer, etc., and an input device such as a keyboard, mouse, etc., a processor (e.g., a CPU, a μCPU, etc.) and computer readable storage medium ("memory") such as physical memory like a memory storage device, etc. In one instance, the console 316 allows an operator to select and/or perform a scan such as an axil scan, e.g., a 360-degree cone beam axial scan, a less than 360-degree cone beam axial scan, and/or other scan, and generate volumetric image data free of certain cone beam artifacts.

A subject support 318, such as a couch, supports an object or subject in the examination region 308. The subject support 318 is movable in coordination with performing an imaging procedure so as to guide the subject or object with respect to the examination region 308 for loading, scanning, and/or unloading the subject or object.

Figure 4:
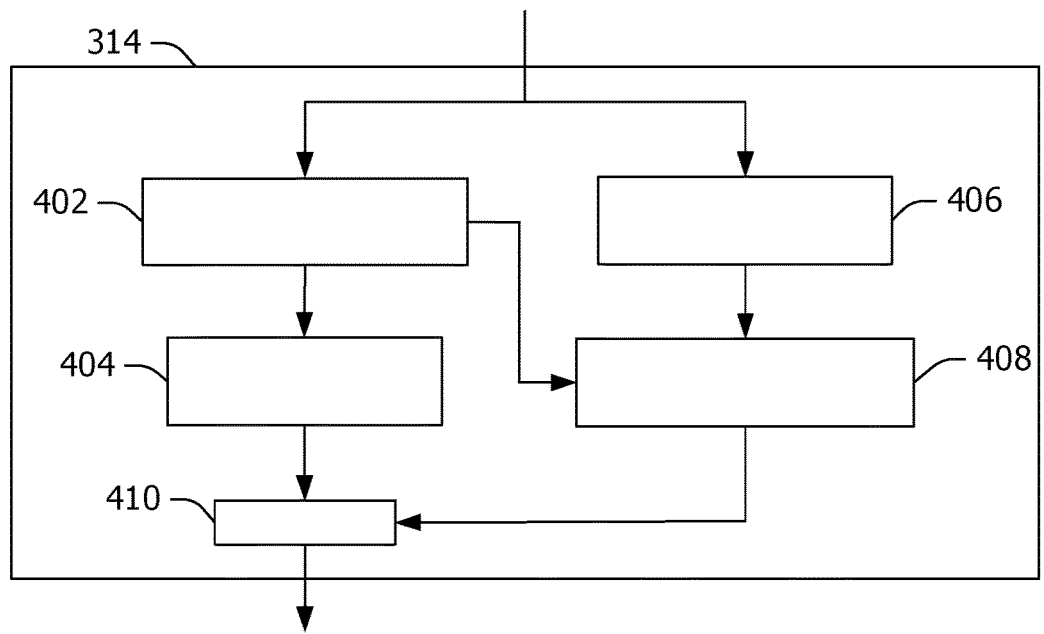
FIG. 4 diagrammatically illustrates an example of the reconstructor for a 360-degree scan, in accordance with an embodiment(s) herein.

FIG. 4 diagrammatically illustrates an example of the reconstructor 314 configured to process cone beam projection data from a 360-degree scan. The reconstructor 314 receives, as input, the 360-degree projection data from the 360-degree scan.

A redundancy weight processor 402 applies a redundancy weighting for a short scan reconstruction (i.e., less than all of the 360-degree projection data) to the projection data from the 360-degree scan. This may include applying a Parker-Weighting and/or other redundancy weighting to only a subset of the projection data from the 360-degree scan. Example redundancy weighting is discussed in Koken et al., "Aperture weighted cardiac reconstruction for cone-beam CT," Physics in Medicine and Biology, 51(14), 3433-3448, (2006). Other approaches are also contemplated herein.

A short-scan reconstructor 404 is configured to reconstruct the redundancy weighted 360-degree projection data to produce short scan volumetric image data. As described herein, where variation of the cone angle of the rays used in backprojecting into a particular voxel results in higher frequencies along the (z) axis of rotation not being weighted properly in all regions of the 3-D Fourier domain, and the mis-weighting of certain frequencies manifests as cone beam artifacts in the reconstructed short scan volumetric image data.

Figure 5:
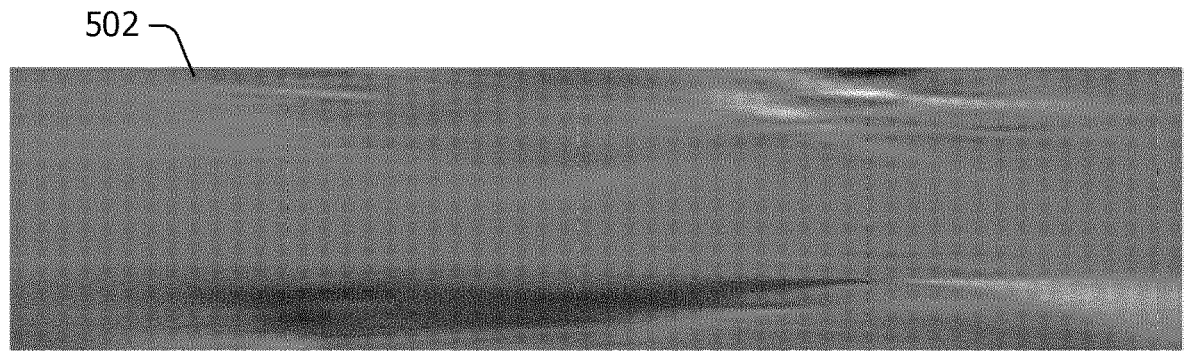
FIG. 5 illustrates an example correction/cone beam artifact image, in accordance with an embodiment(s) herein.

A 360-degree reconstructor 406 is configured to reconstruct all of the projection data from the 360-degree scan to produce 360-degree volumetric image data. A spatially variant 3-D filter 408 filters the 360-degree scan volumetric image data. In the illustrated embodiment, a shape of the spatially variant 3-D filter is based on the redundancy weighting. In one instance, the filtered 360-degree scan volumetric image data represents the cone beam artifact in the short scan volumetric image data. FIG. 5 shows an example correction/cone beam artifact image 502.

Figure 1:
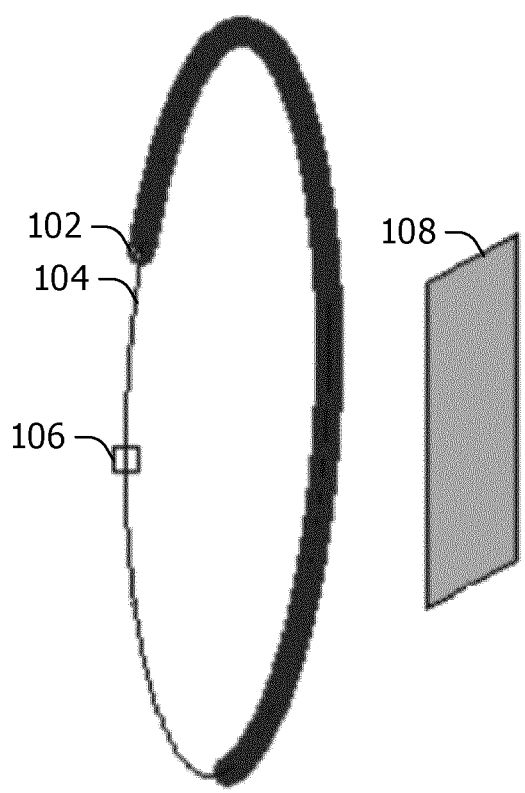
FIG. 1 diagrammatically illustrates imaging where source locations for reconstructing an image are on a circular path of an X-ray source that do not cross an imaging plane.
Figure 2:
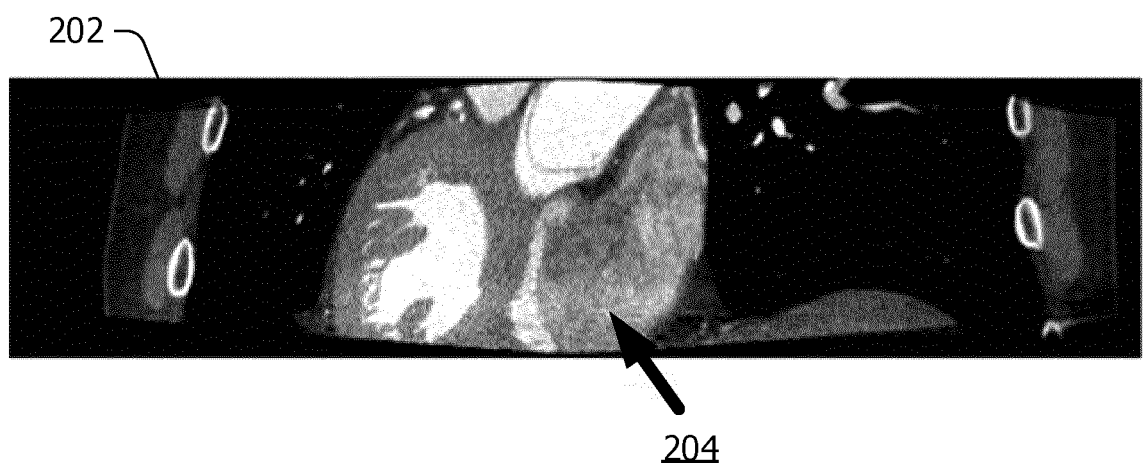
FIG. 2 illustrates an image with cone beam artifact for the imaging of FIG. 1.
Figure 6:
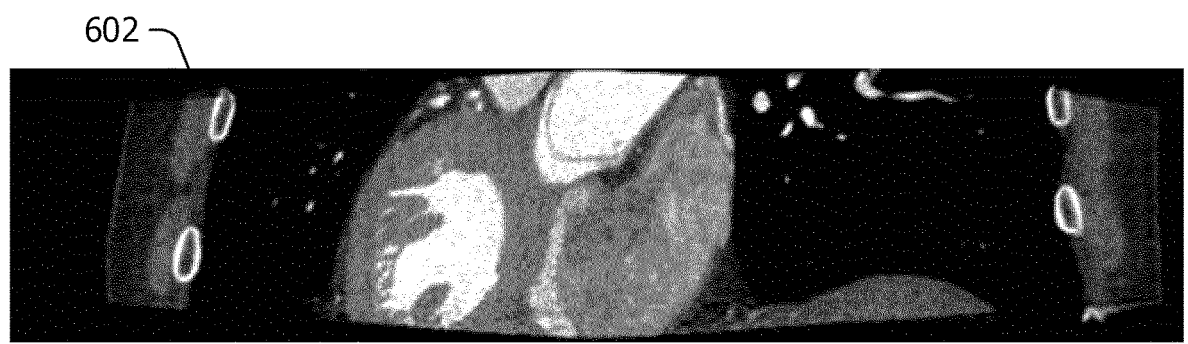
FIG. 6 illustrates an example cone beam artifact corrected image, in accordance with an embodiment(s) herein.

A combiner 410 adds/subtracts the short scan volumetric image data output by the short-scan reconstructor 404 and the cone beam artifact volumetric image data output by the spatially variant 3-D filter 408. The output of the combiner 410 is cone beam artifact corrected short-scan volumetric image data. FIG. 6 shows an example output corrected image 602 resulting from adding the image 202 of FIG. 2 and the correction/cone beam artifact image 502 of FIG. 5. The cone beam artifact corrected short-scan volumetric image data does not include the cone beam artifacts.

The following describes an example of the spatially variant 3-D filter applied by the spatially variant 3-D filter 408.

In this example, $W_k$ represents a desired view-weighting or redundancy weighting to apply to each view k in a 3-D short-scan back-projection. In one instance, $W_k$ is a 1-D vector with weights between 0 and 1 and is constant for all voxels in the reconstructed volume. However, other end points are contemplated herein and/or $W_k$ can vary for different voxels. For sake of brevity, the following describes the case for constant $W_k$ for all voxels.

In one instance, an $N_m \times N_n \times N_p$ matrix $ZW(m, n, p)$ is filled with values representing the effective local frequency weighting for each voxel that is introduced by the view-weighted 3-D back-projection operation. The maximum z-deviations for each z-frequency plane can be expressed as shown in Equation 1:

$$z(p) = -\left(p - \frac{Np}{2}\right) \cdot \frac{z0 * zf}{\frac{Np}{2}},\quad\text{Equation 1}$$

where $p \in \{0: Np-1\}$, z0 is the z-coordinate of a given voxel to be corrected (relative to the z-location of the source in the axial scan), and zf is a scaling factor which scales the maximum cone angle for the current voxel into the frequency domain of the 3-D filter.

For each z-frequency plane p in the 3-D filter ZW, and for each angle in a given set of view angles θ(k), the Cartesian coordinates of a sample projection can be determined by Equations 2 and 3:

$$xp(i,k) = r\text{proj}(i) \cdot \cos(\theta(k)),\text{ and}\quad\text{Equation 2:}$$

$$yp(i,k) = r\text{proj}(i) \cdot \sin(\theta(k)),\quad\text{Equation 3:}$$

where $$rproj(i) = (-2M + 1) + \frac{4M - 2}{2M - 2} \cdot i$$

is the 2-D radial frequency sampling of a projection with 2*M−1 samples, and where $i \in \{0:2*M-2\}$.

The deviation in the x- and y-coordinates caused by the tilting of the plane can be determined by Equations 4 and 5:

$$\text{tilt}_{x(k)} = -\sin(\theta(k)) \cdot z(p),\text{ and}\quad\text{Equation 4:}$$

$$\text{tilt}_{y(k)} = \cos(\theta(k)) \cdot z(p).\quad\text{Equation 5:}$$

A final x- and y-coordinates describing the intersection of the tilted BP plane with the current z-frequency plane are given by Equations 6 and 7:

$$xpt(i,k) = xp(i,k) + \text{tilt}_{x(k)},\text{ and}\quad\text{Equation 6:}$$

$$yPt(i,k) = yp(i,k) + \text{tilt}_{y(k)}.\quad\text{Equation 7:}$$

Four (4) sets of points are defined based on the values of xpt and ypt for each of 4 quadrants of the angles in $\emptyset_k$ as shown in Equations 8, 9 and 10:

$$xw_q = xpt,\ \theta_k \in \left(0, \frac{pi}{2}\right] + \frac{pi}{2} \cdot q,\quad\text{Equation 8}$$

$$yw_q = ypt,\ \theta_k \in \left(0, \frac{pi}{2}\right] + \frac{pi}{2} \cdot q,\text{ and}\quad\text{Equation 9}$$

$$wm_q = W_k,\ \theta_k \in \left(0, \frac{pi}{2}\right] + \frac{pi}{2} \cdot q,\quad\text{Equation 10}$$

with $q \in \{0:3\}$, and the matrices $xw_q$, $yw_q$, and $wm_q$ define a surface $wm_q = F(x, y)$ on a non-uniform sampling of the Cartesian coordinates given by $xw_q$ and $yw_q$. The surface F is interpolated onto a uniformly sampled grid defined by the points XG and YG. An example of such an interpolation is shown in Equation 11:

$$v(m,n)_q = \text{griddata}(xw_q, yw_q, wm_q, XG(m,n), YG(m,n))\quad\text{Equation 11:}$$

where XG and YG are the x- and y-coordinates of a uniform Cartesian grid, given by Equations 12 and 13:

$$XG(m, n) = \left(n - \frac{Nn}{2}\right) \cdot \frac{M}{\frac{Nn}{2}},\text{ and}\quad\text{Equation 12}$$

$$YG(m, n) = \left(m - \frac{Nm}{2}\right) \cdot \frac{M}{\frac{Nm}{2}},\quad\text{Equation 13}$$

with $m \in \{0:Nm-1\}$ and $n \in \{0:Nn-1\}$.

After the re-gridding interpolation, there are four (4) Nm×Nn matrices $v(m, n)_q$ representing the weights contributed by the views in each of the 4 quadrants. These weight matrices are then added together to deliver a final set of weights fw for the current z-frequency plane p, as shown in Equation 14:

$$fw(m,n)_p = \Sigma_q v(m,n,q),\text{ and}\quad\text{Equation 14:}$$

and this above is repeated until all of the z-frequency planes are filled, where $ZW(m, n, p) = fw(m, n)_p$.

The above approach accurately reproduces only the missing or mis-weighted frequencies from the short-scan volumetric image data, for each voxel. The following describes the above in another manner.

Considering a voxel at a particular x-, y-, and z-coordinate within the reconstructed volumetric image data, a subset of "ray-planes," corresponding to a subset of the rays used to backproject into this voxel, are placed within the 3-D Fourier space. For each z-plane in the 3D Fourier domain filter kernel, the intersection of the ray-planes with each z-plane are computed, and a value corresponding to the weight of this ray within the view-weighted reconstruction is added into the z-plane at these intersection points. For regions where the ray-planes overlap, separate summations are taken over different quadrants of angles to prevent interference in the calculations.

Once the entire sub-set of ray-planes has been processed, each z-plane is re-gridded into Cartesian coordinates, and the separate summations added together to yield the final values of the 3-D filter for each z-plane. A 3-D frequency domain filter is built up that consists of the following different kinds of regions: a) regions where weights of the filter w=2; b) regions where 1<w<2; c) regions where w=1; d) regions with 0<w<1, and e) regions with w=0. This filter models the frequency mis-weighting that occurs for a local voxel during the nominal view-weighted short-scan reconstruction. An artifact-producing filter can be generated from the above filter by subtracting one (1) from all filter points, thus passing only the frequencies that are over-weighted (>1) or under-weighted (<1).

FIGS. 7-15 show examples of the frequency domain representation of such a filter for voxels located at isocenter and three (3) different z-offsets from the scan axis.

Figure 7:
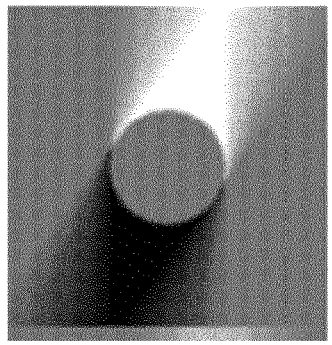
FIGS. 7-15 show several example 3-D spatially variant filters, in accordance with an embodiment(s) herein.
Figure 8:
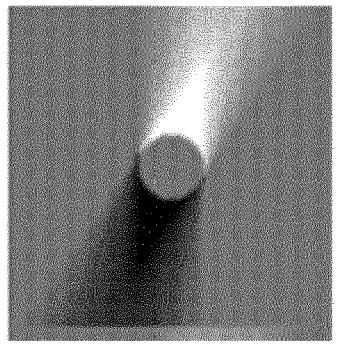
Figure 9:
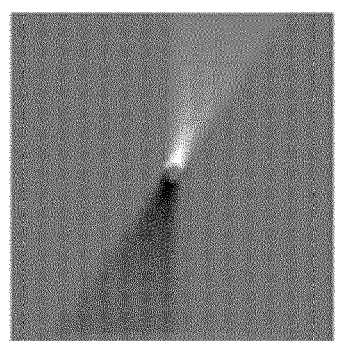

FIG. 7 shows an example 3-D spatially variant (frequency domain) filter for a z-frequency bin 20 (out of 128) for a z-position of twenty-eight millimeters (28 mm) with respect to a source scan axis. FIG. 8 shows an example 3-D spatially variant the filter for the z-frequency bin 20 for a z-position of fifteen millimeters (15 mm) with respect to the source scan axis. FIG. 9 shows an example 3-D spatially variant the filter for the z-frequency bin 20 for a z-position of two and a half millimeters (2.5 mm) with respect to the source scan axis.

Figure 10:
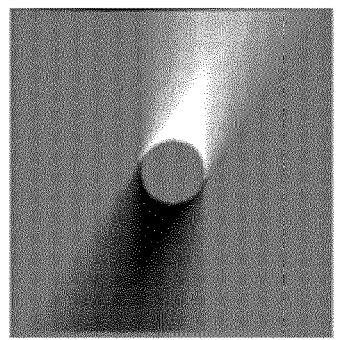
Figure 11:
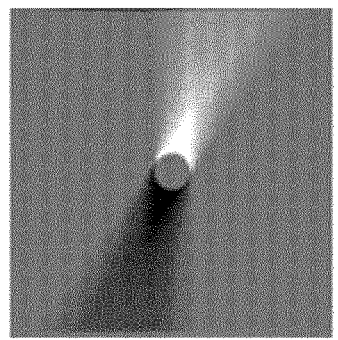
Figure 12:
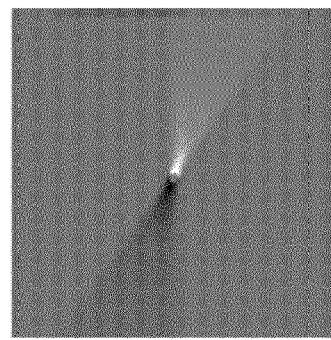

FIG. 10 shows an example 3-D spatially variant (frequency domain) filter for z-frequency bin 40 for the z-position of 28 mm with respect to the source scan axis. FIG. 11 shows an example 3-D spatially variant the filter for the z-frequency bin 40 for the z-position of 15 mm with respect to the source scan axis. FIG. 12 shows an example 3-D spatially variant the filter for the z-frequency bin 40 for the z-position of two and 2.5 mm with respect to the source scan axis.

Figure 13:
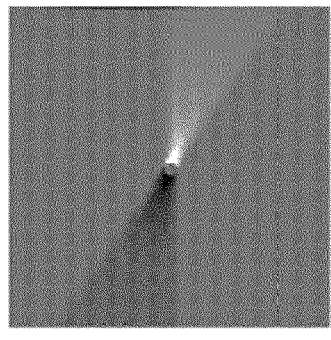
Figure 14:
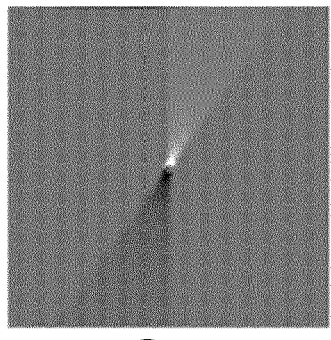
Figure 15:
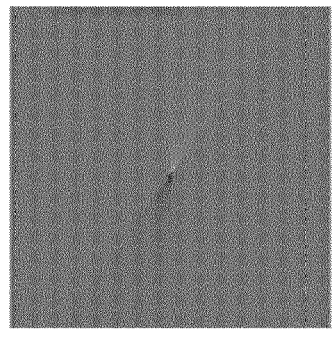

FIG. 13 shows an example 3-D spatially variant (frequency domain) filter for z-frequency bin 60 for the z-position of 28 mm with respect to the source scan axis. FIG. 14 shows an example 3-D spatially variant the filter for the z-frequency bin 60 for the z-position of 15 mm with respect to the source scan axis. FIG. 15 shows an example 3-D spatially variant the filter for the z-frequency bin 60 for the z-position of two and 2.5 mm with respect to the source scan axis.

From FIGS. 7-15, as the distance to the z-axis becomes smaller, the regions of the filter with values not equal to 1 becomes smaller, and thus errors from the frequency mis-weighting (and the cone beam artifacts) will gradually become smaller. This is what happens in a 3-D gated reconstruction. The spatially variant 3D filter can be applied using 3-D FFTs (fast Fourier transforms) and/or otherwise.

Figure 16:
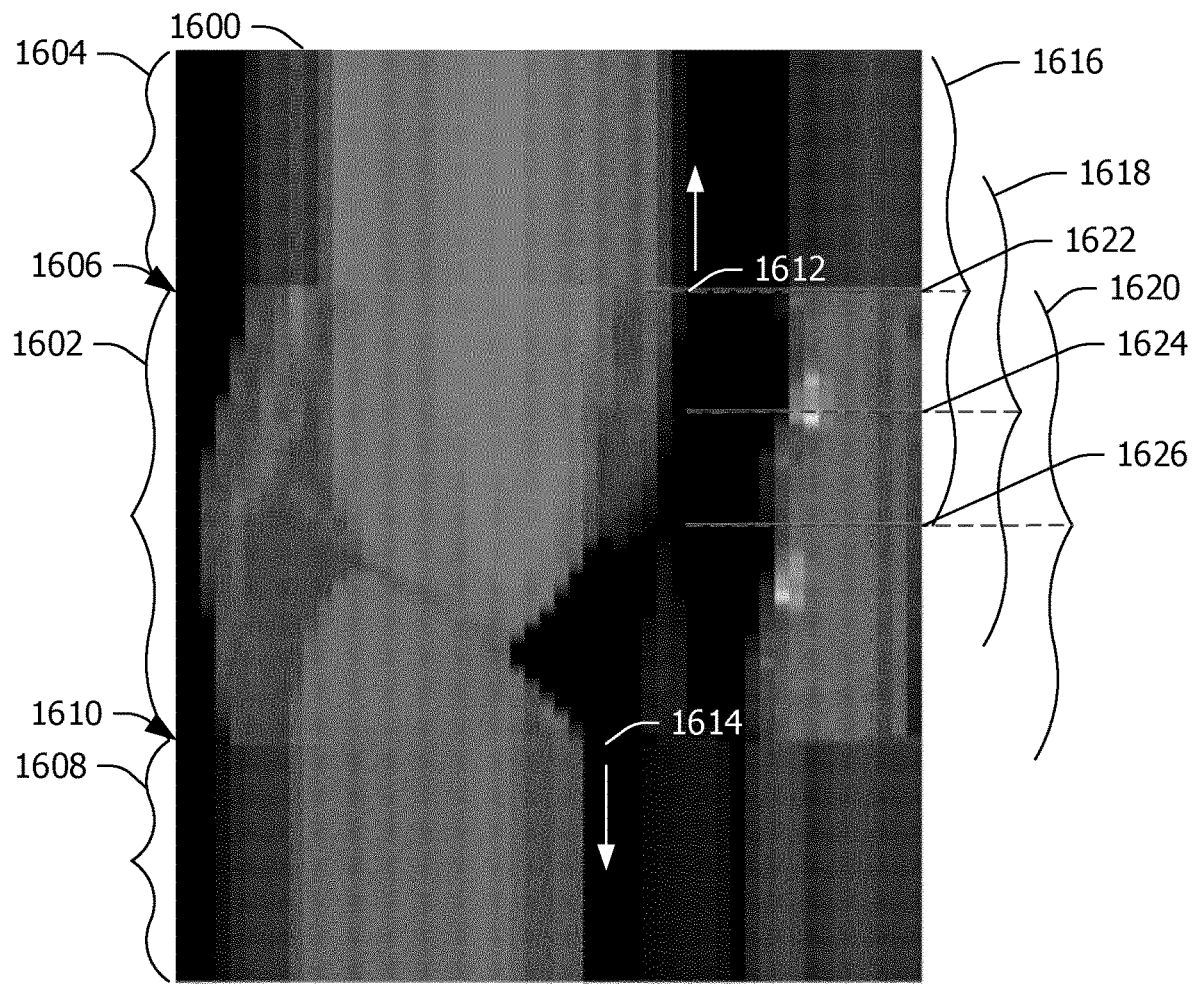
FIG. 16 shows a diagram of a sliding window FFT used to implement the 3-D spatially variant filter, in accordance with an embodiment(s) herein.

In one instance, to avoid problems with circular convolution on a limited number of image slices, the implementation uses a "sliding window" with the first and last slices of the volumetric image data repeated to fill up extrapolated regions for the FFT on the slices at the top and bottom of the volumetric image dat. FIG. 16 shows an example. A coronal image 1600 includes an image 1602 to be corrected, an extrapolated region 1604 at one end 1606, and an extrapolated region 1608 at another end 1610, which opposes the end 1606. The extrapolated region 1604 includes voxel/pixels 1612 at the end 1606 repeated. The extrapolated region 1608 includes voxel/pixels 1614 at the end 1610 repeated. FIG. 16 shows three windows 1616, 1618 and 1620 respectively for correcting voxel/pixels rows 1622, 1624 and 1626 of the image 1602.

Figure 17:
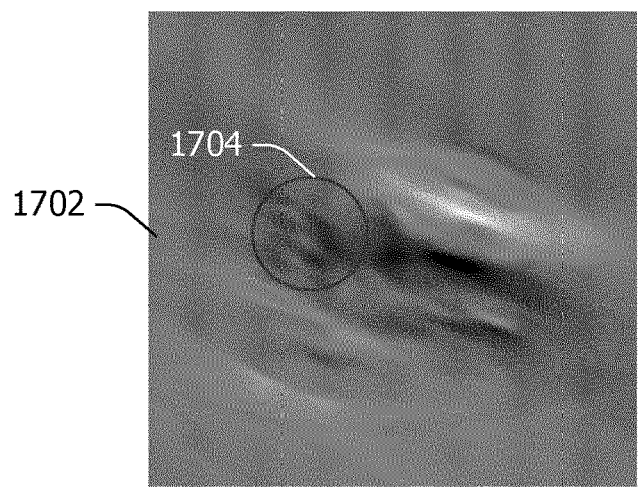
FIG. 17 shows an artifact correction image generated using a directional 2-D filter.
Figure 18:
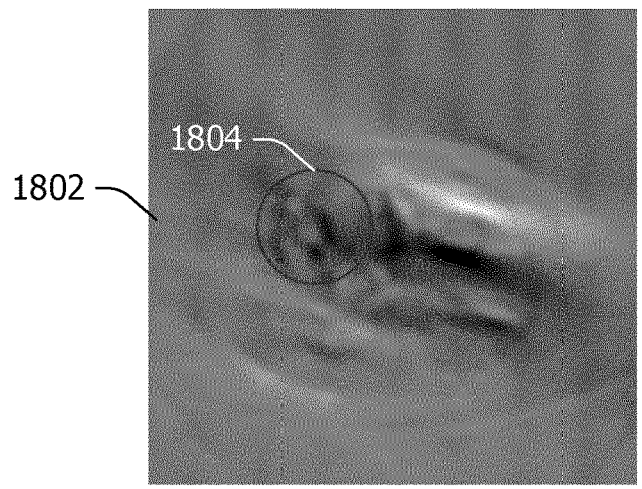
FIG. 18 shows an artifact correction image generated using an isotropic 2-D filter.
Figure 19:
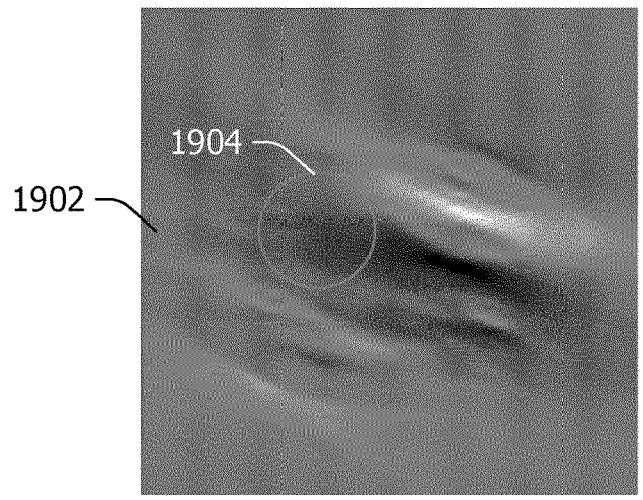
FIG. 19 shows an artifact correction image generated with the spatially variant 3-D filter, in accordance with an embodiment(s) herein.

In one instance, the approached described herein corrects only cone beam artifacts and does not allow other differences into the correction/cone beam artifact image, which can happen when using only a 2-D filter to apply a cone beam correction. By way of example, FIG. 17 shows an artifact correction image 1702 generated using a directional 2-D filter, and FIG. 18 shows an artifact correction image 1802 generated using an isotropic 2-D filter. These approaches respectively allows structure into to the artifact correction image 1702 as shown in the region of interest 1704 and into to the artifact correction image 1802 as shown in the region of interest 1804. FIG. 19 shows an artifact correction image 1902 generated with the spatially variant 3-D filter described herein. The structures in regions of interests 1704 and 1804 are not in a region of interest 904 of the artifact correction image 1902.

The spatially variant 3-D filter has been described in connection with the frequency domain. In a variation, the spatially variant 3-D filter is a spatial domain filter applied in the spatial domain.

The above-described spatially variant 3-D filter is spatially variant only in the z-direction. In a variation, the spatially variant 3-D filter is also spatially variant in x- and/or y-directions.

In a variation, the spatially variant 3-D filter is applied on a down-sampled volume of the initial image, which, in one instance, improves processing speed.

Figure 20:
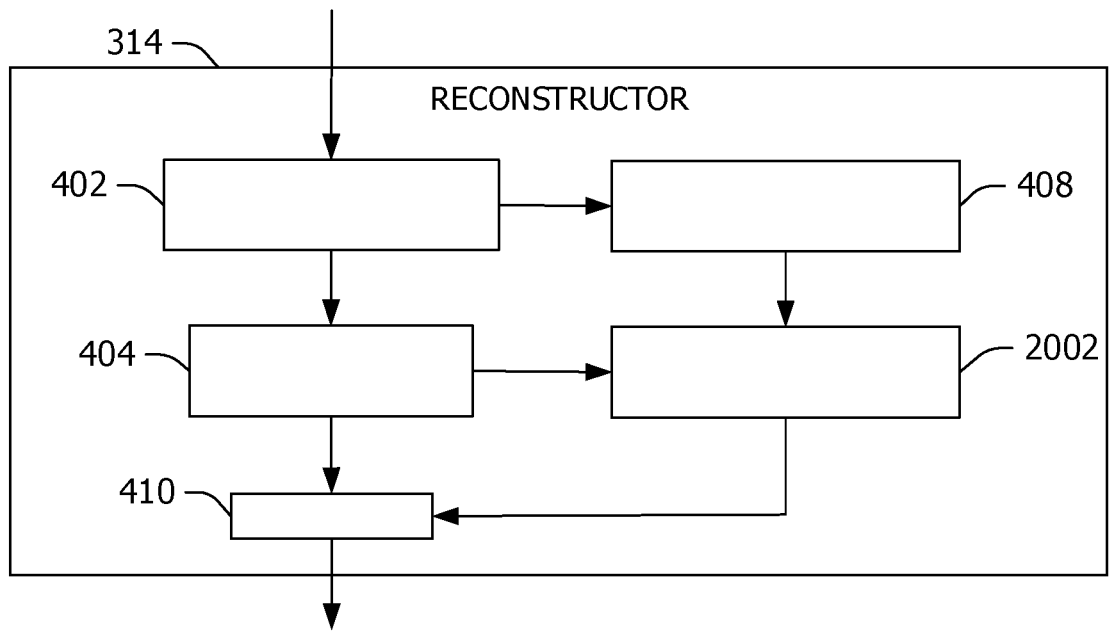
FIG. 20 diagrammatically illustrates an example of the reconstructor for a short (less than 360-degree) scan, in accordance with an embodiment(s) herein.

FIG. 20 diagrammatically illustrates a variation of the reconstructor 314 configured to process projection data from a less than 360-degree (short) scan. Such a short scan, generally, is a lower-dose scan, relative to a 360-degree scan. Additional extrapolation may be needed to estimate portions of the volume which do not see sufficient data for a reconstruction from the short-scan acquisition.

In this example, the redundancy weight processor 402 applies a redundancy weighting for a short scan reconstruction to the short scan projection data, e.g., similar to the redundancy weighting applied in FIG. 20 and/or otherwise. The short-scan reconstructor 404 is configured to reconstruct the redundancy weighted short scan projection data to produce short scan volumetric image data.

Again, as described herein, where variation of the cone angle of the rays used in backprojecting into a particular voxel results in higher frequencies along the (z) axis of rotation not being weighted properly in all regions of the 3-D Fourier domain, and the mis-weighting of certain frequencies manifests as cone beam artifacts in the reconstructed short scan volumetric image data.

In this example, the spatially variant 3-D filter 408 is determined as described herein in connection with FIG. 4 and/or otherwise. The spatially variant 3-D filter 408 is then inverted, and an inverted spatially variant 3-D filter 2002 filters the short scan volumetric image data. In one instance, the inverted spatially variant 3-D filter 2002 re-weights improperly weighted frequencies of the short scan volumetric image data.

The combiner 410 adds/subtracts the short scan volumetric image data output by the short-scan reconstructor 404 and the re-weighted short scan volumetric image data output by the inverted spatially variant 3-D filter 2002. The output of the combiner 410 is cone beam artifact corrected short-scan volumetric image data. The cone beam artifact corrected short-scan volumetric image data does not include the cone beam artifacts.

Figure 21:
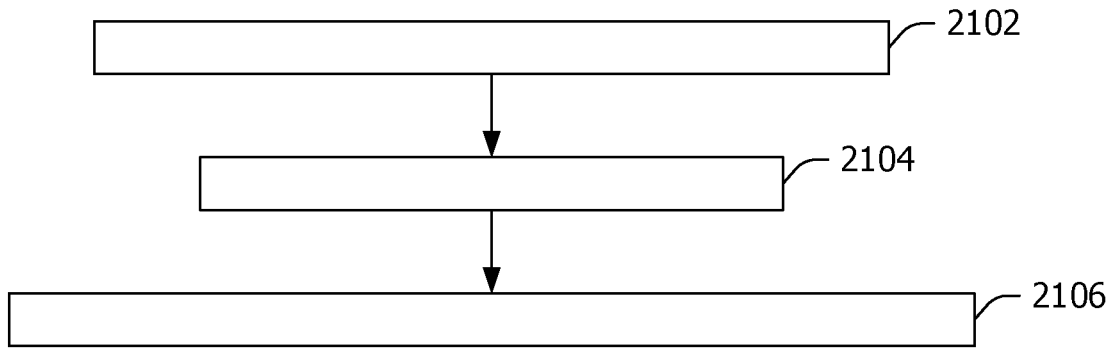
FIG. 21 illustrates an example method for correcting cone beam artifacts in connection with a 360-degree scan, in accordance with an embodiment(s) herein.

FIG. 21 illustrates an example method for correcting cone beam artifacts in connection with a 360-degree scan, in accordance with an embodiment(s) herein. It is to be appreciated that the ordering of the acts in the method is not limiting.

As such, other orderings are contemplated herein. In addition, one or more acts may be omitted, and/or one or more additional acts may be included.

At 2102, cone beam projection data for a 360-degree scan (360-degree cone beam projection data) is obtained, as described herein and/or otherwise.

At 2104, the cone beam projection data is reconstructed to generate volumetric image data, as described herein and/or otherwise.

At 2106, the volumetric image data is corrected for cone beam artifact, as described herein and/or otherwise.

Figure 22:
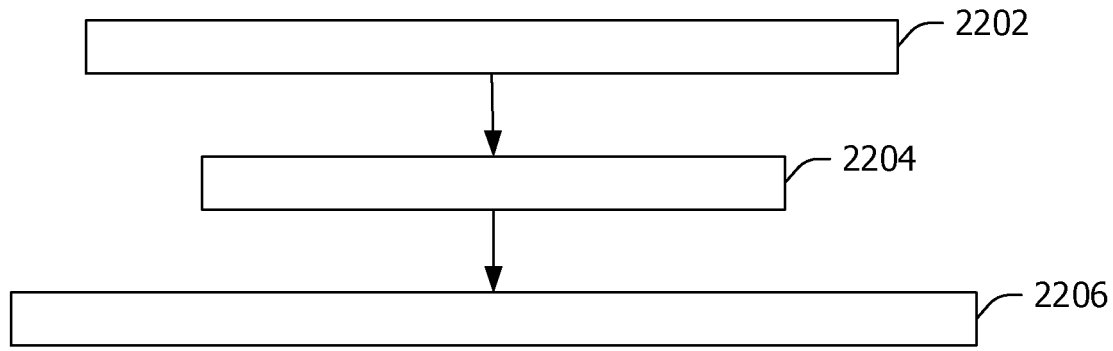
FIG. 22 illustrates an example method for correcting cone beam artifacts in connection with a short scan, in accordance with an embodiment(s) herein.

FIG. 22 illustrates an example method for correcting cone beam artifacts in connection with a short scan, in accordance with an embodiment(s) herein.

It is to be appreciated that the ordering of the acts in the method is not limiting. As such, other orderings are contemplated herein. In addition, one or more acts may be omitted, and/or one or more additional acts may be included.

At 2202, cone beam projection data for a less than 360-degree scan (short scan cone beam projection data) is obtained, as described herein and/or otherwise.

At 2204, the cone beam projection data is reconstructed to generate volumetric image data, as described herein and/or otherwise.

At 2206, the volumetric image data is corrected for cone beam artifact, as described herein and/or otherwise.

The above may be implemented by way of computer readable instructions, encoded or embedded on computer readable storage medium, which, when executed by a computer processor(s), cause the processor(s) to carry out the described acts. Additionally, or alternatively, at least one of the computer readable instructions is carried out by a signal, carrier wave or other transitory medium, which is not computer readable storage medium.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

The word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A medical imaging system, comprising:
   a short-scan reconstructor configured to reconstruct redundancy weighted cone beam projection data to generate initial short scan cone beam volumetric image data, wherein the initial short scan cone beam volumetric image data includes the cone beam artifact;
   a combiner configured to combine the initial short scan cone beam volumetric image data and correction/cone beam artifact volumetric image data to generate cone beam artifact corrected short scan cone beam volumetric image data;
   a redundancy weight processor configured to determine a redundancy weight and apply the redundancy weight to the cone beam projection data to generate the redundancy weighted cone beam projection data; and
   a spatially variant 3-D filter configured to filter the cone beam volumetric image data based on the redundancy weight to generate the correction/cone beam artifact volumetric image data.

2. The medical imaging system of claim 1, wherein the reconstructor further includes:
   a 360-degree reconstructor configured to reconstruct the cone beam projection data to generate 360-degree cone beam volumetric image data.

3. The medical imaging system of claim 1, wherein the cone beam projection data is 360-degree cone beam projection data.

4. The medical imaging system of claim 1, wherein the reconstructor further includes:
   an inverted spatially variant 3-D filter configured to filter the initial short scan cone beam volumetric image data based on the redundancy weight to generate the correction/cone beam artifact volumetric image data.

5. The medical imaging system of claim 1, wherein the cone beam projection data is short scan cone beam projection data.

6. The medical imaging system of claim 1, wherein the reconstructor is configured to correct the initial short scan cone beam volumetric image data for high z-frequency mis-weighting.

7. A medical imaging method, comprising:
   reconstructing, with a short-scan reconstructor, redundancy weighted cone beam projection data to generate initial short scan cone beam volumetric image data, wherein the initial short scan cone beam volumetric image data includes the cone beam artifact;
   combining, with a combiner, the initial short scan cone beam volumetric image data and correction/cone beam artifact volumetric image data to generate cone beam artifact corrected short scan cone beam volumetric image data;
   applying a redundancy weight to the cone beam projection data to generate the redundancy weighted cone beam projection data; and
   filtering, with a spatially variant 3-D filter, the cone beam volumetric image data based on the redundancy weight to generate the correction/cone beam artifact volumetric image data.

8. The medical imaging method of claim 7, further comprising:
   reconstructing, with a 360-degree reconstructor, the cone beam projection data to generate 360-degree cone beam volumetric image data.

9. The medical imaging method of claim 7, wherein the cone beam projection data is 360-degree cone beam projection data.

10. The medical imaging method of claim 7, further comprising:
    filtering, with an inverted spatially variant 3-D filter, the initial short scan cone beam volumetric image data based on the redundancy weight to generate the correction/cone beam artifact volumetric image data.

11. The medical imaging method of claim 7, wherein the cone beam projection data is short scan cone beam projection data.

12. A non-transitory computer-readable medium for storing executable instructions that, when executed, cause the method of claim 7 to be performed.

* * * * *